United States Patent [19]

Hentschel et al.

[11] 4,424,400

[45] Jan. 3, 1984

[54] OLIGOISOBUTYLCYCLOHEXANE, A PROCESS FOR ITS PREPARATION AND ITS USE

[75] Inventors: Karl-Heinz Hentschel; Rolf Dhein, both of Krefeld, Fed. Rep. of Germany

[73] Assignee: Bayer Aktiengesellschaft, Leverkusen, Fed. Rep. of Germany

[21] Appl. No.: 243,418

[22] Filed: Mar. 13, 1981

[30] Foreign Application Priority Data

Mar. 14, 1980 [DE] Fed. Rep. of Germany ....... 3009848

[51] Int. Cl.$^3$ .......................... C07C 5/00; C07C 13/00
[52] U.S. Cl. ..................................... 585/20; 585/254; 568/38; 568/579
[58] Field of Search .................... 585/254, 20; 568/38, 568/579

[56] References Cited

U.S. PATENT DOCUMENTS 3,161,016  12/1964  Smith et al. ...................... 585/20 X
3,925,217  12/1975  Green et al. .

FOREIGN PATENT DOCUMENTS 2209637  10/1972  Fed. Rep. of Germany .
1794018   3/1978  Fed. Rep. of Germany .
1643079   2/1980  Fed. Rep. of Germany .
7727561   9/1977  France .
1438318  12/1973  United Kingdom .

*Primary Examiner*—Paul F. Shaver
*Attorney, Agent, or Firm*—Sprung, Horn, Kramer & Woods

[57] ABSTRACT

An oligoisobutylcyclohexane of the formula:

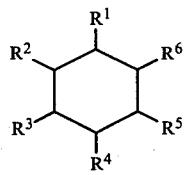

wherein
$R^1$–$R^5$ are identical or different and independently denote hydrogen, a $C_1$–$C_4$- alkyl group, $C_1$–$C_4$-alkoxy group or a $C_1$–$C_4$-alkylthio substitutent and $R^6$ denotes a branched chain $C_{12}$–$C_{40}$-alkyl group of trimeric to decameric isobutene, a process for preparing such oligoisobutylcyclohexanes and their use as dielectric liquids, lubricants, heat transfer media and the like.

9 Claims, No Drawings

OLIGOISOBUTYLCYCLOHEXANE, A PROCESS FOR ITS PREPARATION AND ITS USE

This invention relates to oligoisobutylcyclohexane having a branched chain alkyl substituent derived from oligoisobutene and optionally other substituents on the cyclohexane ring, a process for its preparation, and its use, for example, as a heat transfer medium or dielectric liquid.

1,1,3,3-Tetramethylbutyl-substituted cyclohexane (diisobutylcyclohexane) may be synthesised by various methods. According to J. Amer. Chem. Soc. 75, 937–939 (1953), phenols are reacted with commercial "diisobutene" by a Friedel-Crafts alkylation to form 1,1,3,3-tetramethylbutyl-phenols, which are catalytically hydrogenated to the corresponding cyclohexanols, which in turn are dehydrated to 1,1,3,3-tetramethylbutylcyclohexenes with acid catalysts at high temperatures, and these are finally hydrogenated to the required cyclohexane.

4-Methyl-1-(1,1,3,3-tetramethyl)-butylbenzene, for example, was obtained in a yield of only 4% from p-tolyl magnesium bromide and 2-chloro-2,3,3-trimethylpentane by a Wurtz-Grignard synthesis and then catalytically hydrogenated to 4-methyl-1-(1,1,3,3-tetramethyl)-butyl cyclohexane (see Zh. Obshchei Khim. 27, 2990–2993 (Chemical Abstracts 52, 8064 g, 1957)).

In Izvest. Vysshikh Ucheb. Zavedenii, Khim. i. Khim. Tekhnol. 4 657–660 (1961) (Chemical Abstracts 56, 7182 c) it has been disclosed that the two compounds mentioned above can be obtained in higher yields by a Friedel-Crafts alkylation of toluene in the presence of anhydrous aluminium chloride and nitrobenzene.

It has now been found that the hitherto unknown cyclohexane compounds containing a branched chain alkyl group which is derived from a relatively high molecular weight "oligoisobutene" such as tri- or tetra-isobutene can be obtained by Friedel-Crafts alkylation of aromatic compounds with trimeric to decameric isobutene followed by hydrogenation.

The present invention provides oligoisobutylcyclohexane corresponding to Formula (I):

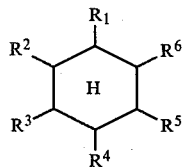

wherein $R^1$–$R^5$ are identical or different and denote hydrogen or a $C_1$–$C_4$-alkyl, $C_1$–$C_4$-alkoxy or $C_1$–$C_4$-alkylthio substituent and $R^6$ denotes a branched chain $C_{12}$–$C_{40}$ alkyl group derived from trimeric to decameric isobutene.

In the formula set forth above, $R^6$ represents a branched alkyl group of a trimeric to decameric isobutene. Such branched alkyl group is generally one obtained by adding a hydrogen, especially a terminal hydrogen atom, from trimeric to decameric isobutene.

Preferred oligoisobutylcyclohexanes of Formula (I) are those in which $R^6$ is a group represented by Formula (2) or (3):

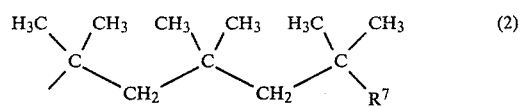

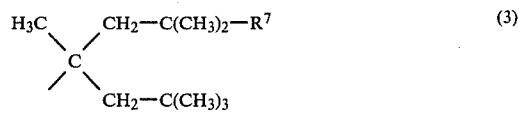

in which $R^7$ denotes a methyl group of the group

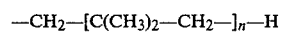

and n is an integer of from 1 to 7, preferably from 1 to 3.

Oligoisobutylcyclohexane corresponding to Formula (4):

wherein $R^6$ has the meaning indicated above is particularly preferred.

Preparation of the compounds according to the invention is carried out in two stages. A mononuclear, optionally substituted aromatic compound is first alkylated with "oligomeric isobutene", e.g. with commercial triisobutene, in the presence of Friedel-Crafts catalysts, and the reaction product is then hydrogenated.

By the term "oligomeric isobutene", there is meant in particular trimeric to decameric isobutene. These trimeric to decameric isobutenes or mixtures thereof, are used for the alkylation.

Oligoisobutenes, e.g. triisobutylene or tetraisobutylene, may be prepared by known methods of oligomerisation of isobutene in the presence of Friedel-Crafts catalysts or Lewis acids. Suitable catalysts include, for example, sulphuric acid or acid aluminas (Chem. Ber. 63 (1930), 104) and $BF_3$/kieselguhr or $BF_3$/aluminium oxide (Dokl. Akad. SSSR 119 (1958), 720, 722, 957, 959). The oligoisobutene obtained is generally a mixture of isomeric olefins. According to J. Amer. Chem. Soc. 63 (1941), 2035, so-called "triisobutylene", for example, consists mainly of 2,2,4,6,6-pentamethyl-hept-3-ene and 2,2,6,6-tetramethyl-4-methyleneheptane as well as small proportions of 2,4,4,6,6-pentamethyl-hept-2-ene and 2,4,4,6,6-pentamethyl-hept-1-ene.

Both isomeric mixtures of isobutenes ranging from triisobutene to decaisobutene and mixtures of these homologous oligoisobutenes with each other may be used for alkylation. Tri-, tetra-, penta- and hexa-isobutene are preferred. Triisobutene and its isomeric mixtures are particularly preferred.

Suitable aromatic compounds for the preparation of the compounds according to the invention are those corresponding to Formula (5):

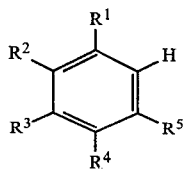

wherein R¹-R⁵ are identical or different and denote hydrogen, or a $C_1$-$C_4$-alkyl, $C_1$-$C_4$-alkoxy or $C_1$-$C_4$-alkylthio substituent.

The following are examples: benzene and alkyl substituted benzenes such as toluene, o-, m- and p-xylene, pentamethylbenzene, ethylbenzene, diethylbenzenes, methyl ethyl benzenes, dimethyl ethyl benzenes, cumene, diisopropyl benzenes, triisopropyl benzenes, cymenes, n-butyl-benzene, iso-butylbenzene, secondary and tertiary butyl benzene, phenyl ethers and phenyl thioethers such as anisole and phenetol, dimethoxybenzenes and phenyl-methyl sulphide. Benzene and $C_1$-$C_4$ monoalkyl substituted benzene, in particular toluene, are preferred.

The usual Friedel-Crafts catalysts such as, for example, hydrofluoric acid, sulphuric acid, polyphosphoric acid, phosphoric acid, aluminum trichloride, iron-(III) chloride, antimony-(V) chloride, tin-(IV) chloride, boron trifluoride, titanium tetrachloride and zirconium tetrachloride may be used for alkylating the aromatic compounds.

Modified Friedel-Crafts catalysts which have been mixed with aliphatic or aromatic nitro compounds, such as nitro methane or nitrobenzene, to enhance the catalytic activity are preferred. A modified catalyst of aluminum trichloride and nitromethane is particularly preferred.

Hydrogenation of the alkylated aromatic compounds may be carried out in known manner. According to the process of invention the hydrogenation is preferably carried out in the presence of a hydrogenation catalyst, such as nickel (e.g. Raney nickel), platinum, palladium or rhenium. In general, the hydrogenation is carried out in the temperature range of 150° to 250° C., preferably 200° to 250° C., and in the pressure range of 150 to 300 atm. The catalyst is generally employed in an amount of 0.1 to 10 percent by weight, preferably 0.5 to 5 percent by weight, relativ to the total amount of the reaction mixture.

The oligoisobutylcyclohexanes according to the invention may be used as heat transfer media and dielectric liquids, e.g. transformer oils, and for the preparation of photographic emulsions.

Compounds of invention can be used as lubricants for traction drive.

The following Example illustrates the invention and describes the preparation and characteristic properties of a representative example of the compounds according to the invention.

EXAMPLE

A modified Friedel-Crafts catalyst is prepared by stirring 266.7 g of anhydrous aluminum trichloride into 366 g of absolute nitromethane, and the catalyst is introduced into 721.2 g of absolute toluene. A mixture of 329.3 g of triisobutene and 180.3 g of absolute toluene is slowly added dropwise within one hour with stirring and the reaction mixture is stirred for a further 4 hours at 20° to 40° C.

The reaction mixture is then poured on 1 liter of ice water and the organic phase is separated off, washed with 500 g of 10% aqueous sodium carbonate solution and then with distilled water until the reaction is neutral, and dried over $CaCl_2$. It is then fractionally distilled in a water jet vacuum.

Yield: 265 g (52% of the theoretical yield, not optimised).

Boiling point (10 Torr): 74° C.

Refractive index: $n_D^{20}=1.4912$ 1280 g of the "isododecyltoluene" (this is in general the para-isomere) prepared by the process described above, containing an "isododecyl" group derived from triisobutene, are hydrogenated with the aid of 4% by weight of a nickel catalyst in an autoclave, first for 75 minutes at a hydrogen pressure of from 150 to 230 atmospheres while the temperature rises from 24° C. to 205° C., then for 475 minutes at a hydrogen pressure of 215 to 280 atmospheres at 205° to 235° C., and finally for 30 minutes at a hydrogen pressure of 275 atmospheres at 235° C.

When the product is subsequently distilled under vacuum, 940 g of a main fraction distilling at 60° to 63° C./10 Torr are obtained (71.8% of the theoretical yield). This fraction has the following properties:

Kinematic viscosities: 20° C. 2.27 mm²s; 37.8° C. (100° F.) 1.64 mm²/s; 98.9° C. (210° F.) 0.83 mm²/s.

Solidification point: $<-70°$ C. $n_D^{20}=1.4464$.

What is claimed is:

1. An oligoisobutylcyclohexane of the formula:

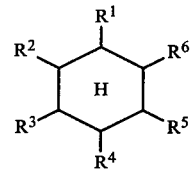

wherein

R¹-R⁵ are identical or different and independently denote hydrogen, a $C_1$-$C_4$-alkyl group, $C_1$-$C_4$-alkoxy group or a $C_1$-$C_4$-alkylthio substituent and R⁶ denotes a branched chain $C_{12}$-$C_{40}$-alkyl group of trimeric to decameric isobutene.

2. An oligoisobutylcyclohexane according to claim 1, wherein R⁶ denotes:

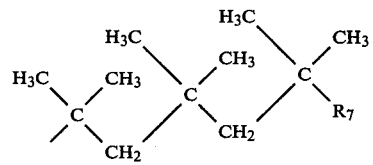

or

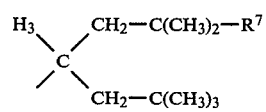

wherein

R⁷ denotes a methyl group or the group $-CH_2-[C(CH_3)_2-CH_2-]_n-H$ and n represents an integer of from 1 to 7.

3. An oligoisobutylcyclohexane according to claim 2 corresponding to:

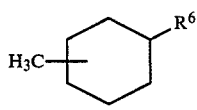

wherein
R⁶ denotes:

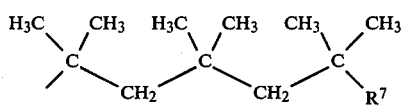

or

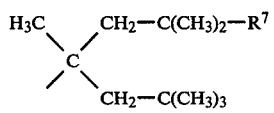

wherein
R⁷ denotes a methyl group or the group —CH₂—[C(CH₃)₂—CH₂]ₙ—H and n represents an integer of from 1 to 3.

4. A process for the preparation of an oligoisobutylcyclohexane according to claim 1, which comprises contacting an aromatic compound of the forumula:

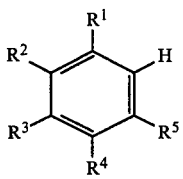

wherein
R₁–R₅ are identical or different and independently denote hydrogen, a C₁–C₄-alkyl substituent, a C₁–C₄-alkoxy substituent or a C₁–C₄-alkylthio substituent with an alkylating agent in the presence of a a Friedel-Crafts catalyst and thereafter hydrogenating the resultant compound.

5. A process according to claim 4, wherein said Friedel-Crafts catalyst is one which has been contacted with an aromatic or aliphatic nitro compound.

6. A process according to claim 5, wherein said Friedel-Crafts catalyst is aluminum trichloride which has been contacted with nitromethane.

7. A process according to claim 6, wherein toluene is alkylated with triisobutene or an isomeric mixture containing the same.

8. A process according to claim 4, wherein the alkylating agent is an oligomeric isobutene.

9. A process according to claim 8, wherein said oligomeric isobutene is trimeric to decameric iosobutene.

* * * * *